(12) United States Patent
Park et al.

(10) Patent No.: US 11,527,773 B2
(45) Date of Patent: Dec. 13, 2022

(54) LITHIUM BATTERY

(71) Applicants: Samsung Electronics Co., Ltd., Suwon-si (KR); Samsung SDI Co., Ltd., Yongin-si (KR)

(72) Inventors: Insun Park, Suwon-si (KR); Myongchun Koh, Hwaseong-si (KR); Dongyoung Kim, Yongin-si (KR); Jinah Seo, Seoul (KR); Yeonji Chung, Yongin-si (KR)

(73) Assignee: SAMSUNG SDI CO., LTD., Gyeonggi-do (KR)

( * ) Notice: Subject to any disclaimer, the term of this patent is extended or adjusted under 35 U.S.C. 154(b) by 362 days.

(21) Appl. No.: 16/663,647

(22) Filed: Oct. 25, 2019

(65) Prior Publication Data

US 2020/0136174 A1 Apr. 30, 2020

(30) Foreign Application Priority Data

Oct. 26, 2018 (KR) .................. 10-2018-0129340

(51) Int. Cl.
*H01M 10/0525* (2010.01)
*C07C 211/21* (2006.01)
(Continued)

(52) U.S. Cl.
CPC ....... *H01M 10/0525* (2013.01); *C07C 211/21* (2013.01); *C07F 5/04* (2013.01);
(Continued)

(58) Field of Classification Search
CPC .. H01M 10/0564–0569; H01M 2300/00–0097
See application file for complete search history.

(56) References Cited

U.S. PATENT DOCUMENTS

| | | | |
|---|---|---|---|
| 8,551,661 B2 | 10/2013 | Amine et al. | |
| 2003/0157407 A1* | 8/2003 | Kosuzu | H01M 4/134 429/231.95 |

(Continued)

FOREIGN PATENT DOCUMENTS

| | | |
|---|---|---|
| CN | 102593516 A | 7/2012 |
| CN | 103401019 A | 11/2013 |

(Continued)

OTHER PUBLICATIONS

Machine translation of JP10-112421 (Year: 1998).*

(Continued)

*Primary Examiner* — Eric R Smith
(74) *Attorney, Agent, or Firm* — Cantor Colburn LLP

(57) ABSTRACT

A lithium battery including: a cathode; an anode; and an electrolyte between the cathode and the anode, wherein the cathode includes a cathode active material represented by Formula 1,

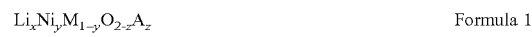
Formula 1 wherein $0.95 \leq x \leq 1.2$, $0.75 \leq y \leq 0.98$, and $0 \leq z < 0.2$,
M is Al, Mg, Mn, Co, Fe, Cr, V, Ti, Cu, B, Ca, Zn, Zr, Nb, Mo, Sr, Sb, W, Bi, or a combination thereof, and
A is an element having an oxidation number of $-1$, $-2$, or $-3$,
wherein each element of M is independently present in an amount of $0.02 \leq y \leq 0.3$,
wherein a total content of M is $0.02 \leq y \leq 0.3$;
and
wherein the electrolyte includes a lithium salt, a non-aqueous solvent, and a diallyl compound represented by Formula 2,

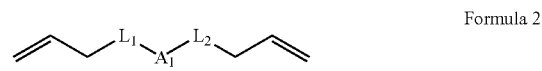
Formula 2 wherein $L_1$ and $L_2$ are each independently a single bond, a $C_1$-$C_{20}$ alkylene group, or a substituted or unsubstituted $C_2$-$C_{20}$ alkenylene group.

20 Claims, 2 Drawing Sheets

(51) Int. Cl.

| | |
|---|---|
| *C07F 5/04* | (2006.01) |
| *C07F 7/08* | (2006.01) |
| *C07F 9/6574* | (2006.01) |
| *H01M 4/505* | (2010.01) |
| *H01M 4/525* | (2010.01) |
| *H01M 10/0567* | (2010.01) |
| *H01M 10/0568* | (2010.01) |
| *H01M 10/0569* | (2010.01) |
| *H01M 4/02* | (2006.01) |

(52) U.S. Cl.
CPC ........ *C07F 7/0805* (2013.01); *C07F 9/65742* (2013.01); *H01M 4/505* (2013.01); *H01M 4/525* (2013.01); *H01M 10/0567* (2013.01); *H01M 10/0568* (2013.01); *H01M 10/0569* (2013.01); *H01M 2004/028* (2013.01); *H01M 2300/0025* (2013.01)

(56) References Cited

U.S. PATENT DOCUMENTS

| | | | |
|---|---|---|---|
| 2006/0147809 A1* | 7/2006 | Amine | H01M 10/0568 429/330 |
| 2010/0015514 A1 | 1/2010 | Miyagi et al. | |
| 2012/0171579 A1 | 7/2012 | Tsai et al. | |
| 2013/0136997 A1 | 5/2013 | An et al. | |
| 2016/0218392 A1 | 7/2016 | Lee et al. | |
| 2016/0293997 A1* | 10/2016 | Yamauchi | H01M 10/0525 |
| 2018/0026304 A1 | 1/2018 | Yokomizo et al. | |
| 2018/0261885 A1 | 9/2018 | Lee et al. | |

FOREIGN PATENT DOCUMENTS

| | | | | |
|---|---|---|---|---|
| EP | 3416229 A1 * | 12/2018 | ........ | H01M 10/0568 |
| JP | 1996236155 A | 9/1996 | | |
| JP | 10112421 A * | 4/1998 | | |
| JP | 2004087459 A | 3/2004 | | |
| JP | 2005267911 A | 9/2005 | | |
| JP | 2007165297 A | 6/2007 | | |
| KR | 19990017135 A | 9/2005 | | |
| KR | 1203666 B1 | 11/2012 | | |
| KR | 1548851 B1 | 9/2015 | | |
| KR | 1633961 B1 | 6/2016 | | |
| KR | 20170128218 A | 11/2017 | | |

OTHER PUBLICATIONS

European Search Report for European Patent Application No. 19205031.8 dated Feb. 28, 2020.

Markus Dobbelin et al., "Synthesis of Pyrrolidinium-Based Poly(ionic liquid) Electrolytes with Poly(ethylene glycol) Side Chains", Chemistry of materials, Mar. 30, 2012, pp. 1583-1590, vol. 24.

Qinfeng Zheng et al. "N-Allyl-N,N-Bis(trimethylsilyl)amine as a Novel Electrolyte Additive to Enhance the Interfacial Stability of a Ni-Rich Electrode for Lithium-Ion Batteries", Appled Materials & Interfaces, Apr. 24, 2018, pp. 16843-16851, vol. 10.

* cited by examiner

LITHIUM BATTERY

CROSS-REFERENCE TO RELATED APPLICATION

This application claims priority to and the benefit of Korean Patent Application No. 10-2018-0129340, filed on Oct. 26, 2018, in the Korean Intellectual Property Office, and all the benefits accruing therefrom under 35 U.S.C. § 119, the content of which is incorporated herein in its entirety by reference.

BACKGROUND

1. Field

The present disclosure relates to a lithium battery.

2. Description of the Related Art

Lithium batteries are used as power sources for portable electronic appliances such as video cameras, mobile phones, and notebook computers. Rechargeable lithium secondary batteries have three times the energy density per unit weight than conventional lead batteries, nickel-cadmium batteries, nickel metal hydride batteries and nickel-zinc batteries. Rechargeable lithium secondary batteries may also be charged at higher speeds.

To manufacture a lithium second battery having high energy density, a cathode active material, which provides an increased discharge capacity, may be used. A cathode active material may also have relatively low electrochemical stability. Therefore, a side reaction between a cathode active material and an electrolyte may occur during a charge-discharge process of a lithium secondary battery. As a result, stability of the lithium secondary battery may deteriorate. Therefore, there is a need for a method of improving the stability of a lithium secondary battery, said battery including a cathode active material that provides an increased discharge capacity.

SUMMARY

Provided is an improved lithium battery.

Additional aspects will be set forth in part in the description which follows and, in part, will be apparent from the description, or may be learned by practice of the presented embodiments.

According to an aspect of an embodiment, a lithium battery includes: a cathode; an anode; and an electrolyte between the cathode and the anode, wherein the cathode includes a cathode active material represented by Formula 1,

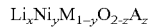  Formula 1 wherein $0.9 \leq x \leq 1.2$, $0.7 \leq y \leq 0.98$, and $0 \leq z < 0.2$,

M is Al, Mg, Mn, Co, Fe, Cr, V, Ti, Cu, B, Ca, Zn, Zr, Nb, Mo, Sr, Sb, W, Bi, or a combination thereof, and A is an element having an oxidation number of −1, −2, or −3, wherein each element of M is independently present in an amount of $0.02 \leq y \leq 0.3$, wherein an total content of M is $0.025 \leq y \leq 0.3$; and wherein the electrolyte includes a lithium salt, a non-aqueous solvent, and a diallyl compound represented by Formula 2,

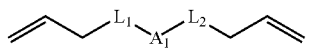  Formula 2 wherein $L_1$ and $L_2$ are each independently a single bond, a $C_1$-$C_{20}$ alkylene group, or a substituted or unsubstituted $C_2$-$C_{20}$ alkenylene group, $A_1$ is —NH— or —Si($R_1$)($R_2$)—, and $R_1$ and $R_2$ are each independently a hydrogen atom, a substituted or unsubstituted linear or branched $C_1$-$C_{30}$ alkyl group, a substituted or unsubstituted $C_2$-$C_{20}$ alkenyl group, a substituted or unsubstituted $C_2$-$C_{20}$ vinyl group, a substituted or unsubstituted $C_2$-$C_{20}$ allyl group, or a substituted or unsubstituted $C_6$-$C_{60}$ aryl group.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
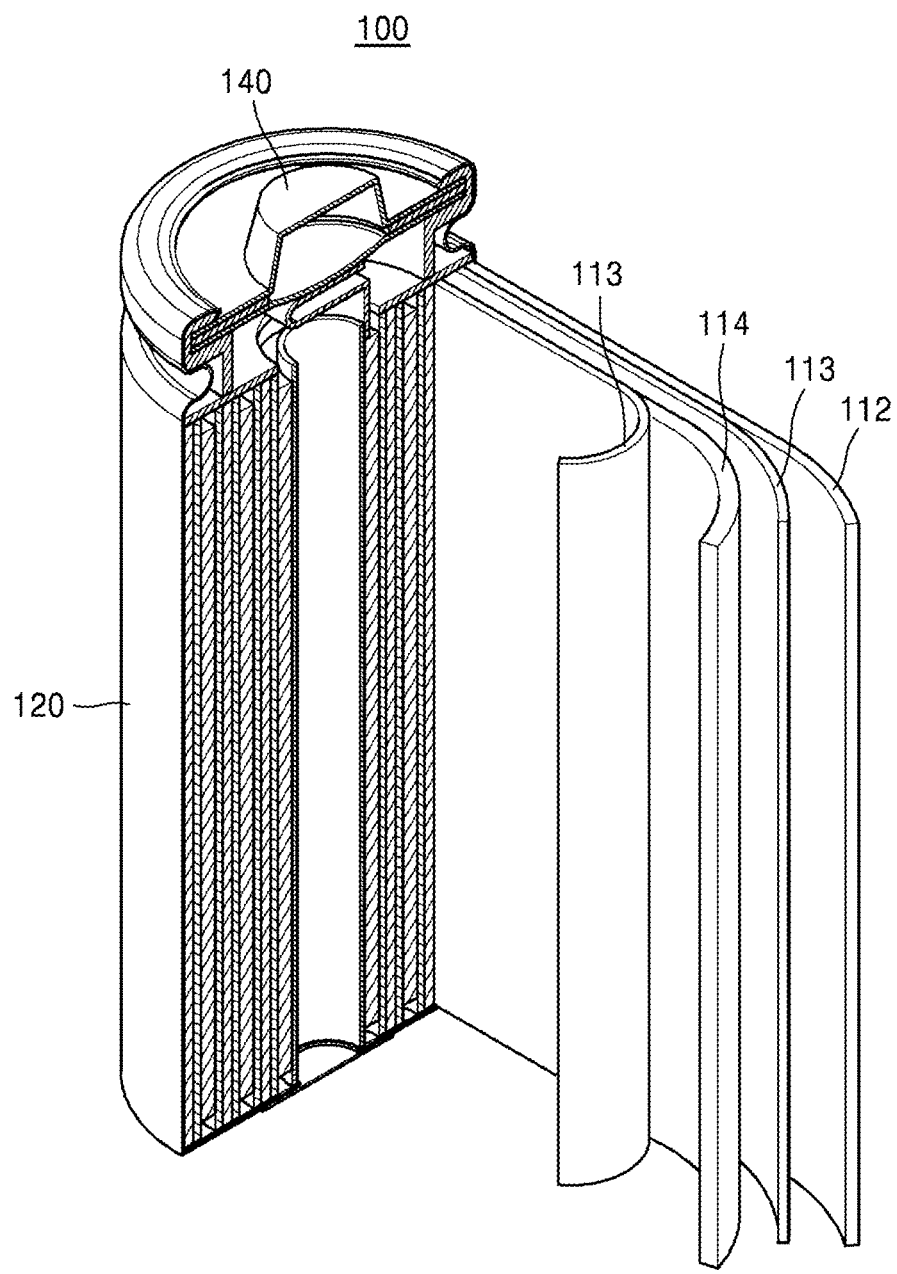
FIG. 1 is a schematic view of an embodiment of a lithium battery.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain various aspects.

As used herein, the term "and/or" includes any and all combinations of one or more of the associated listed items. Expressions such as "at least one of," when preceding a list of elements, modify the entire list of elements and do not modify the individual elements of the list. Hereinafter, it will be understood that "on" may include not only being directly on, but also being in a non-contacting manner. Thus when an element is referred to as being "on" another element, it can be directly on the other element, or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. The singular forms "a," "an" and "the" are intended to include the plural forms as well, unless the context clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Also, when a portion "includes" an element, another element may be further included, rather than excluding the existence of the other element, unless otherwise described.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Also, operations of all methods described herein may be performed in any suitable order unless otherwise indicated herein or otherwise clearly contradicted by context. The disclosure is not limited to the described order of the operations. The use of any and all examples, or exemplary language provided herein, is intended merely to better illuminate the disclosure and shall not be construed to pose a limitation on the scope of the disclosure unless otherwise claimed.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless defined otherwise, all terms (including technical and scientific terms) in the specification may be defined as commonly understood by one having ordinary skilled in the art. The terms defined in a generally-used dictionary may not be interpreted ideally or exaggeratedly unless clearly defined. In addition, unless explicitly described to the contrary, the word "comprise" and variations such as "comprises" or "comprising," will be understood to imply the inclusion of stated elements but not the exclusion of any other elements.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, an organic electrolyte for lithium batteries and a lithium battery employing the organic electrolyte according to example embodiments will be described in more detail.

A lithium battery according to an embodiment includes: a cathode; an anode; and an electrolyte between the cathode and the anode, wherein the cathode includes a cathode active material represented by Formula 1, $$Li_xNi_yM_{1-y}O_{2-z}A_z \qquad \text{Formula 1}$$

wherein $0.9 \leq x \leq 1.2$, $0.7 \leq y \leq 0.98$, and $0 \leq z < 0.2$,

M is Al, Mg, Mn, Co, Fe, Cr, V, Ti, Cu, B, Ca, Zn, Zr, Nb, Mo, Sr, Sb, W, Bi, or a combination thereof, and A is an element having an oxidation number of −1, −2, or −3, wherein each element of M is independently present in an amount of $0.02 \leq y \times 0.3$, wherein an total content of M is $0.02 \leq y \leq 0.3$; and wherein the electrolyte includes a lithium salt, a non-aqueous solvent, and a diallyl compound represented by Formula 2,

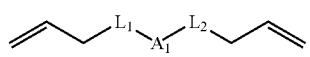

Formula 2 wherein $L_1$ and $L_2$ are each independently a single bond, a $C_1$-$C_{20}$ alkylene group, or a substituted or unsubstituted $C_2$-$C_{20}$ alkenylene group, $A_1$ is —NH— or —Si($R_1$)($R_2$)—, and $R_1$ and $R_2$ are each independently a hydrogen atom, a substituted or unsubstituted linear or branched $C_1$-$C_{30}$ alkyl group, a substituted or unsubstituted $C_2$-$C_{20}$ alkenyl group, a substituted or unsubstituted $C_2$-$C_{20}$ vinyl group, a substituted or unsubstituted $C_2$-$C_{20}$ allyl group, or a substituted or unsubstituted $C_6$-$C_{60}$ aryl group.

When a lithium metal composite oxide includes a high nickel (Ni) content, like the cathode active material represented by Formula 1 above, a high-power and high-capacity battery may be realized. However, metal cations such as $Ni^{3+}$ cations contained in the lithium metal composite oxide are eluted from the cathode into the electrolyte, thus causing the deterioration of the cathode. The metal cations may react with a passivation film, e.g., a solid electrolyte interphase (SEI) film, of the anode to decompose the SEI film, expose a part of the anode active material to the electrolyte, and cause a side reaction, thereby deteriorating capacity characteristics and lifetime characteristics while increasing the gas generation.

It has now been surprisingly discovered that, when the lithium battery includes an electrolyte including the diallyl compound represented by Formula 2, the side reaction caused by $Ni^{3+}$ cations is minimized, thereby reducing the generation of gas and improving the lifetime of the lithium battery.

More specifically, because the diallyl compound is attracted to the $Ni^{3+}$ cations, inclusion of the diallyl compound in the battery may suppress the side reaction caused by the $Ni^{3+}$ cations. In particular, even when the lithium battery is driven under a high voltage, the diallyl compound maintains attraction to the $Ni^{3+}$ cations, and thus may suppress the decomposition of the SEI film. Further, the diallyl compound may be reduced and decomposed at a metal anode prior to a solvent, and because the structure of a product thereof after reduction and decomposition is stable, a more stable SEI film may be formed. The SEI film formed on the surface of the anode reduces the generation of gas due to a side reaction, thereby improving the electrochemical characteristics of the lithium battery. Consequently, the diallyl compound improves the stability of the SEI film, thereby reducing the gas generation of a lithium secondary battery and improving the performance of the lithium battery.

The amount of the diallyl compound in the electrolyte may be about 5 parts by weight or less per 100 parts by weight of the electrolyte, but is not limited thereto. The amount thereof may not be limited as long as $Ni^{3+}$ cations eluted from the cathode active material into the electrolyte are stabilized and a protective film is suitably formed on the surface of the anode by the diallyl compound. When the amount of the diallyl compound is more than about 5 parts by weight, the diallyl compound itself may be greatly decomposed to increase coating resistance, and the produced $CO_2$ may deteriorate battery capacity, storage stability, and cycle characteristics.

According to an embodiment, the amount of the diallyl compound may be about 0.05 parts by weight to about 5 parts by weight per 100 parts by weight of the electrolyte. For example, the amount of the diallyl compound may be about 0.1 parts by weight to about 3 parts by weight, about 0.2 parts by weight to about 3 parts by weight, or about 0.5 parts by weight to about 2 parts by weight per 100 parts by weight of the electrolyte.

When the amount of the diallyl compound is less than 0.05 parts by weight, the protective film may not be formed, and it may be difficult to obtain a sufficient resistance reduction effect.

According to an embodiment, the $L_1$ and $L_2$ may each independently be a methylene group, an ethylene group, a propylene group, an isobutylene group, a sec-butylene group, a ter-butylene group, a pentylene group, a 2-pentylene group, a 3-pentylene group, a 2,2-dimethylpropylene group, a 2-methylbutylene group, a 2-methyl-2-butylene group, a 3-methylbutylene group, a 3-methyl-2-butylene group, a hexylene group, a 2-hexylene group, a 3-hexylene group, a 2-methylpentylene group, a 2-methyl-2-pentylene group, 2-methyl-3-pentylene group, a 3-methylpentylene group, a 3-methyl-3-pentylene group, a 4-methylpentylene group, a 4-methyl-2-pentylene group, a 3-dimethyl-2-butylene group, a 3,3-dimethylbutylene group, a 3,3-dimethyl-2-butylene group, or a 2-ethylbutylene group.

According to an embodiment, the $R_1$ and $R_2$ may each independently be a substituted or unsubstituted linear or branched $C_1$-$C_{30}$ alkyl group, a substituted or unsubstituted $C_2$-$C_{20}$ alkenyl group, a substituted or unsubstituted $C_2$-$C_{20}$ vinyl group, a substituted or unsubstituted $C_2$-$C_{20}$ allyl group, or a substituted or unsubstituted $C_6$-$C_{60}$ aryl group.

According to another embodiment, the $R_1$ and $R_2$ may each independently be a phenyl group, a naphthyl group, an anthracenyl group, a biphenyl group, and a terphenyl group; and a phenyl group, a naphthyl group, an anthracenyl group, a biphenyl group, and a terphenyl group, each of which is substituted with at least one selected from a methyl group, an ethyl group, a propyl group, an isopropyl group, a butyl group, a sec-butyl group, a tert-butyl group, or an isobutyl group.

Examples of the $C_1$-$C_{30}$ alkyl group may include, but are not limited to, a methyl group, an ethyl group, a propyl group, an isopropyl group, a butyl group, a sec-butyl group, a tert-butyl group, and an isobutyl group.

The $C_2$-$C_{20}$ vinyl group refers to a substituent group of $C_2$-$C_{20}$ including a vinyl group ($-CH=CH_2$).

Examples of the $C_6$-$C_{60}$ aryl group may include, but are not limited to, a phenyl group, a biphenyl group, and a terphenyl group.

According to an embodiment, the diallyl compound may be a compound represented by Formula 3, Formula 4, or a combination thereof.

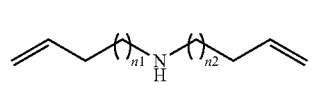

Formula 3

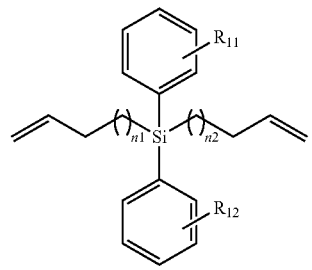

Formula 4

In Formulae 3 and 4, n1 and n2 may each independently be an integer of 0 to 5; and $R_{11}$ and $R_{12}$ may each independently be a hydrogen atom, a methyl group, an ethyl group, a propyl group, an isopropyl group, a butyl group, a sec-butyl group, a tert-butyl group, or an isobutyl group.

For example, the diallyl compound may be a compound represented by Formula 5, Formula 6, or a combination thereof.

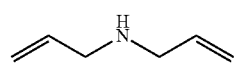

Formula 5

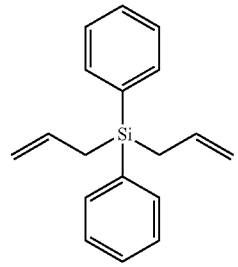

Formula 6

Since the allyl compound represented by Formula 2 has a high reduction potential due to the double bond included in an allyl group, the gas generation of the lithium battery may be reduced. In addition, the structure of a product after reduction and decomposition by an $A_1$ moiety may be stabilized to form a stable passivation film (e.g., SEI film) on the surface of the anode to protect the anode. Accordingly, lifetime characteristics of the lithium battery may be improved.

The electrolyte may include a lithium salt. The lithium salt may be dissolved in an organic solvent, may act as a supply source of lithium ions in the lithium battery, and for example, may promote the migration of lithium ions between the anode and the cathode.

The anion of the lithium salt included in the electrolyte may be $PF_6^-$, $BF_4^-$, $SbF_6^-$, $AsF_6^-$, $C_4F_9SO_3^-$, $ClO_4^-$, $AlO_2^-$, $AlCl_4^-$, $C_xF_{2x+1}SO_3^-$ (wherein, x is a natural number), $(C_xF_{2x+1}SO_2)(C_yF_{2y+1}SO_2)N^-$ (wherein, x and y are natural numbers), a halide, or a combination thereof.

The lithium salt included in the electrolyte may include $LiPF_6$, $LiBF_4$, $LiCF_3SO_3$, $Li(CF_3SO_2)_2N$, $LiC_2F_5SO_3$, $Li(FSO_2)_2N$, $LiC_4F_9SO_3$, $LiN(SO_2CF_2CF_3)_2$, a compound represented by Formulae 22 to 25, or a combination thereof.

Formula 22

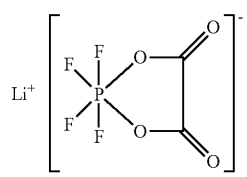

Formula 23

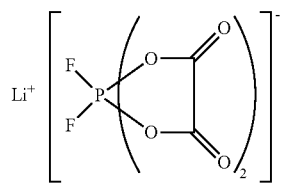

Formula 24

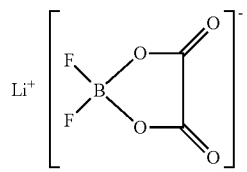

Formula 25

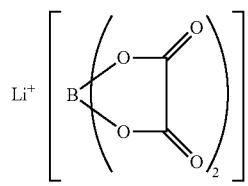

The concentration of the lithium salt may be about 0.01 molar (M) to about 5.0 M, about 0.05 M to about 5.0 M, about 0.1 M to about 5.0 M, or about 0.1 M to about 2.0 M, but is not limited to these ranges. Suitable concentrations for use in a lithium battery electrolyte may be used.

The amount of the lithium salt in a solvent-free electrolyte may be about 0.001 parts by weight to about 30 parts by weight per 100 parts by weight of the solvent-free electrolyte, but is not limited to this range. The amount thereof is not limited as long as the electrolyte may effectively transfer lithium ions and/or electrons during a charge-discharge process.

The amount of the lithium salt in a solvent-containing electrolyte may be about 100 millimolar (mM) to about 10M. For example, the amount thereof may be about 100 mM to about 2 M. For example, the amount thereof may be about 500 mM to about 2 M. However, the amount thereof is not limited to these ranges. The amount thereof is not limited as long as the electrolyte may effectively transfer lithium ions and/or electrons during a charge-discharge process.

According to an embodiment, the concentration of the lithium salt in the electrolyte may be about 1.1 M to about 2.5 M. For example, the concentration of the lithium salt may be about 1.15 M to about 2.2 M, or about 1.3 M to about 2 M.

The non-aqueous solvent may be a carbonate containing solvent, an ester containing solvent, an ether containing solvent, a ketone containing solvent, a nitrile containing solvent, an aprotic solvent, or a combination thereof.

As the carbonate containing solvent, dimethyl carbonate (DMC), diethyl carbonate (DEC), ethyl methyl carbonate (EMC), dipropyl carbonate (DPC), methyl propyl carbonate (MPC), ethyl propyl carbonate (EPC), ethylene carbonate (EC), propylene carbonate (PC), butylene carbonate (BC), or tetraethylene glycol dimethyl ether (TEGDME) may be used. As the ester containing solvent, methyl acetate, ethyl acetate, n-propyl acetate, dimethylacetate, methyl propionate (MP), ethyl propionate, γ-butyrolactone, decanolide, valerolactone, mevalonolactone, or caprolactone may be used. As the ether containing solvent, dibutyl ether, tetraglyme, diglyme, dimethoxyethane, 2-methyltetrahydrofuran, or tetrahydrofuran may be used. As the ketone containing solvent, cyclohexanone may be used. As the nitrile containing solvent, acetonitrile (AN), succinonitrile (SN), or adiponitrile may be used.

The aprotic solvent may be used alone or in a mixture of two or more other solvents. When the aprotic solvent is used in a mixture of two or more other solvents, the mixing ratio may be suitably adjusted depending on battery performance.

As other solvents, dimethylsulfoxide, dimethylformamide, dimethylacetamide, or tetrahydrofuran may be used, but the solvents are not limited thereto. Any suitable organic solvent for use in a lithium battery may be used.

For example, the non-aqueous solvent may include about 50 volume percent (vol %) to about 95 vol % of chain carbonate and about 5 vol % to about 50 vol % of cyclic carbonate, about 55 vol % to about 95 vol % of chain carbonate and about 5 vol % to about 45 vol % of cyclic carbonate, about 60 vol % to about 95 vol % of chain carbonate and about 5 vol % to about 40 vol % of cyclic carbonate, about 65 vol % to about 95 vol % of chain carbonate and about 5 vol % to about 35 vol % of cyclic carbonate, or about 70 vol % to about 95 vol % of chain carbonate and about 5 vol % to about 30 vol % of cyclic carbonate. For example, the non-aqueous solvent may be a mixed solvent of three or more kinds of non-aqueous solvents.

In some cases, the non-aqueous solvent may further include fluoro-ethylene carbonate (FEC), vinylene carbonate (VC), vinyl ethylene carbonate (VEC), a phosphorus (P) containing compound, or a sulfur (S) containing compound.

For example, the non-aqueous solvent may include fluoro-ethylene carbonate (FEC). For example, the lithium secondary battery may include the FEC in an amount of about 0.1 vol % to about 10 vol % based on the total volume of the non-aqueous solvent. For example, the lithium secondary battery may include the FEC in an amount of about 0.5 vol % to about 7 vol % based on the total volume of the non-aqueous solvent. For example, the lithium secondary battery may include the FEC in an amount of about 1 vol % to about 7 vol % based on the total volume of the non-aqueous solvent. For example, the lithium secondary battery may include the FEC in an amount of about 2 vol % to about 7 vol % based on the total volume of the non-aqueous solvent. When the FEC is included in the non-aqueous solvent within the above range, an effective SEI film that does not inhibit the diffusion speed of lithium ions may be rapidly formed.

According to an embodiment, the non-aqueous solvent may be dimethyl carbonate (DMC), diethyl carbonate (DEC), ethyl methyl carbonate (EMC), dipropyl carbonate (DPC), methyl propyl carbonate (MPC), ethyl propyl carbonate (EPC), methyl ethyl carbonate (MEC), ethylene carbonate (EC), propylene carbonate (PC), butylene carbonate (BC), methyl propionate (MP), ethyl propionate (EP), propyl propionate (PP), tetraethylene glycol dimethyl ether (TEGDME), or a combination thereof.

The electrolyte may include a carbonate containing a carbon-carbon single or multiple bond, a carboxylic acid anhydride containing a carbon-carbon single or multiple bond, or a combination thereof. The multiple bond may be a double bond or a triple bond, and the carbonate and the carboxylic acid anhydride may be linear or cyclic.

According to an embodiment, the electrolyte may include a cyclic carbonate compound, a cyclic acid anhydride compound, a phosphorus (P) containing compound, a sulfur (S) containing compound, or a combination thereof.

According to an embodiment, the electrolyte may include a cyclic carbonate compound, a cyclic acid anhydride compound, or a combination thereof. Here, the reduction potential of the diallyl compound is higher than the reduction potential of the cyclic carbonate compound or the cyclic acid anhydride compound.

According to an embodiment, the amount of the cyclic carbonate compound, the cyclic acid anhydride compound or the combination thereof may be about 0.1 parts by weight to about 30 parts by weight, for example, 0.1 parts by weight to about 2 parts by weight, per 100 parts by weight of the electrolyte.

The cyclic carbonate compound may be, for example, fluoro-ethylene carbonate (FEC), vinylene carbonate (VC), vinyl ethylene carbonate (VEC), or a combination thereof.

The cyclic acid anhydride compound may be, for example, maleic anhydride, succinic anhydride, or a combination thereof.

The phosphorus-containing compound may be, for example, a phosphine compound, a phosphate compound, a phosphite compound, or a combination thereof.

Examples of the phosphine compound may include, but are not limited to, triphenylphosphine or tris(4-fluorophenyl)phosphine, tris(2,4-difluorophenyl)phosphine, and tris (perfluorophenyl)phosphine. Examples of the phosphate compound may include, but are not limited to, triphenyl phosphate (TPPa) and trimethyl phosphate (TMPa). Examples of the phosphite compound may include, but are not limited to, triethylphosphite (TEPi), trimethylphosphite, tripropylphosphite, tributylphosphite, tris (trimethylsilyl) phosphite, and triphenylphosphite.

The sulfur-containing compound may be, for example, a sulfone compound, a sulfonate compound, a sultone compound, a disulfonate compound, or a combination thereof.

Examples of the sulfone compound may include, but are not limited to, ethyl methyl sulfone, divinyl sulfone, and tetramethylene sulfone. Examples of the sulfonate compound may include, but are not limited to, methyl methane sulfonate, ethyl methane sulfonate, and diallyl sulfonate. Examples of the disulfonate compound may include, but are not limited to, methylene methane disulfonate (MMDS) and busulfan. Examples of the sultone compound may include, but are not limited to, fluoropropane sultone (FPS).

According to an embodiment, the electrolyte may be included in the lithium battery in an amount of about 1 gram per ampere-hour (g/Ah) to about 3 g/Ah.

The cathode may include a cathode active material represented by Formula 1 above.

For example, in Formula 1, A may be halogen, S, or N, but is not limited thereto.

In Formula 1, y indicates the amount of Ni in the cathode active material. According to an embodiment, in Formula 1, y may satisfy $0.8 \leq y \leq 0.98$.

Further, according to an embodiment, in Formula 1, M may be Co, Mn, or a combination thereof.

For example, the cathode may include $Li_{1.02}Ni_{0.80}Co_{0.15}Mn_{0.05}O_2$, $Li_{1.02}Ni_{0.85}Co_{0.1}Mn_{0.05}O_2$, $Li_{1.02}Ni_{0.88}Co_{0.08}Mn_{0.04}O_2$, $Li_{1.02}Ni_{0.88}Co_{0.10}Mn_{0.02}O_2$, $Li_{1.02}Ni_{0.91}Co_{0.06}Mn_{0.03}O_2$, $LiNi_{0.94}Co_{0.04}Mn_{0.02}O_2$, $Li_{1.02}Ni_{0.80}Co_{0.15}Al_{0.05}O_2$, $Li_{1.02}Ni_{0.85}Co_{0.1}Al_{0.05}O_2$, $Li_{1.02}Ni_{0.88}Co_{0.08}Al_{0.04}O_2$, $Li_{1.02}Ni_{0.88}Co_{0.10}Al_{0.02}O_2$, $Li_{1.02}Ni_{0.91}Co_{0.06}Al_{0.03}O_2$, $LiNi_{0.94}Co_{0.04}Al_{0.02}O_2$, or a combination thereof.

According to an embodiment, in Formula 1, y may satisfy $0.88 \leq y \leq 0.98$.

For example, the cathode active material may be represented by Formula 7, Formula 8, or a combination thereof.

$$Li_{x'}Ni_{y'}Co_{1-y'-z'}Al_{z'}O_2 \qquad \text{Formula 7}$$

$$Li_{x'}Ni_{y'}Co_{1-y'-z'}Mn_{z'}O_2 \qquad \text{Formula 8}$$

In Formulae 7 and 8, x', y', and z' are each independently $0.9 \leq x' \leq 1.2$, $0.88 \leq y' \leq 0.98$, $0 < z' < 0.1$, and $0 < 1-y'-z' < 0.12$.

For example, the cathode may include $Li_{1.02}Ni_{0.88}Co_{0.08}Mn_{0.04}O_2$, $Li_{1.02}Ni_{0.88}Co_{0.10}Mn_{0.02}O_2$, $Li_{1.02}Ni_{0.91}Co_{0.06}Mn_{0.03}O_2$, $LiNi_{0.94}Co_{0.04}Mn_{0.02}O_2$, $LiNi_{0.88}Co_{0.10}Mn_{0.02}O_2$, $LiNi_{0.88}Co_{0.08}Mn_{0.04}O_2$, $Li_{1.02}Ni_{0.88}Co_{0.08}Al_{0.04}O_2$, $Li_{1.02}Ni_{0.88}Co_{0.10}Al_{0.02}O_2$, $Li_{1.02}Ni_{0.91}Co_{0.06}Al_{0.03}O_2$, $LiNi_{0.94}Co_{0.04}Al_{0.02}O_2$, or a combination thereof.

As described above, in the case of a battery comprising a lithium nickel oxide, lifetime characteristics of the battery may deteriorate with the increase in the amount of $Ni^{3+}$ cations.

Furthermore, a lithium battery wherein an anode active material comprises a metal alloyable with lithium or a carbon containing component, may allow the generation of gas by catalysis at high temperature and the deterioration of lifetime characteristics due to the generation of the gas.

As described above, when FEC, VC, VEC, MA, SA, the phosphorus (P) containing compound, or the sulfur (S) containing compound is included in the above range, passivation may occur involving the chemical reaction product of these materials, that is, an SEI film may be formed on a part or all of the surface of the anode. In this case, the diallyl compound is reduced by a double bond included in an allyl group. Accordingly, a compound such as FEC in the passivation film may be protected, a strong SEI film may be formed, and gas generation may be prevented during high-temperature storage, thereby realizing improvements in the stability and performance of the lithium battery.

Further, the cathode may comprise lithium cobalt oxide, lithium nickel cobalt manganese oxide, lithium nickel cobalt aluminum oxide, lithium iron oxide, lithium manganese oxide, or a combination thereof, in addition to the above-described anode active material. However, the present disclosure is not limited thereto, and the anode may further include any cathode active materials suitable for use in a lithium battery.

The anode may include an anode active material. The anode active material may include a silicon containing compound, a carbon containing compound, a composite of a silicon containing compound and a carbon containing compound, and a silicon oxide of formula $SiO_{x1}$, wherein $0<x1<2$. For example, the anode may include an anode active material including a metal alloyable with lithium, a silicon containing anode active material, and/or a carbon containing anode active material.

For example, the silicon containing compound may include silicon particles, and the average diameter of the silicon particles may be 200 nanometers (nm) or less.

For example, the carbon containing compound may include graphite.

For example, a composite of a silicon containing compound and a carbon containing compound may be a composite having a structure in which silicon nanoparticles are arranged on a carbon containing compound, a composite having a structure in which silicon particles are included on the surface of the carbon containing compound and inside the carbon containing compound, or a composite having a structure in which silicon particles are coated with the carbon containing compound and included inside the carbon containing compound. The composite of a silicon containing compound and a carbon containing compound may be an active material obtained by dispersing silicon nanoparticles having an average particle diameter of about 200 nm or less on carbon containing compound particles and then carbon-coating the resulting particles, or an active material in which silicon particles exist on graphite and inside graphite. The average particle diameter of secondary particles of the composite of the silicon containing compound and the carbon containing compound may be about 5 micrometers (μm) to about 20 μm, and the average particle diameter of the silicon nanoparticles may be 200 nm or less, 150 nm or less, 100 nm or less, 50 nm or less, 20 nm or less, 10 nm or less. For example, the average particle diameter of the silicon nanoparticles may be about 100 nm to about 150 nm.

For example, the capacity of the composite of the silicon containing compound and the carbon containing compound may be about 300 mAh/g to about 700 mAh/g. For example, the capacity of the composite of the silicon containing compound and the carbon containing compound may be about 400 mAh/g to about 600 mAh/g.

The capacity retention of the lithium battery at 25° C. after 200 cycles of charging and discharging may be 75% or more, for example, 82% or more. For example, when the anode of the lithium battery includes graphite, the capacity retention of the lithium battery at 25° C. after 200 cycles of charging and discharging may be 80% or more.

The DCIR (Direct Current Internal Resistance) increase of the lithium battery at 25° C. after 200 cycles of charging and discharging may be 180% or less. For example, when the anode of the lithium battery includes graphite, the DCIR increase of the lithium battery at 25° C. after 200 cycles of charging and discharging may be 150% or less, for example, 120% or less.

The cell energy density of the lithium battery per unit cell volume may be 500 watt-hours per liter (Wh/L) or more. The lithium battery may provide improved output by providing a high energy density of 500 Wh/L or more.

The lithium battery is not limited in form, and includes a lithium ion battery, a lithium ion polymer battery, and a lithium sulfur battery.

The lithium secondary battery according to an embodiment may be manufactured by the following method.

First, a cathode is prepared.

For example, a cathode active material composition, in which a cathode active material, a conductive agent, a binder, and a solvent are mixed, may be prepared. The cathode is prepared by coating a cathode current collector with the cathode active material composition. Alternatively, the cathode may be prepared by casting the cathode active material composition onto a separate support, separating a film from the support, and then laminating the separated film on a metal current collector. The cathode is not limited to the above-described form, and may have a form other than the above-described form.

The cathode active material may include a lithium-containing metal oxide in addition to the cathode active material represented by Formula 1 above. As the lithium-containing metal oxide, for example, two or more kinds of composite oxides of lithium and a metal selected from cobalt, manganese, nickel, and combinations thereof may be used.

For example, the cathode active material may comprise $Li_aA_{1-b}B'_bD_2$ (wherein, $0.90 \le a \le 1.8$ and $0 \le b \le 0.5$); $Li_a E_{1-b}B'_bO_{2-c}D_c$ (wherein, $0.90 \le a \le 1.8$, $0 \le b \le 0.5$, and $0 \le c \le 0.05$); $LiE_{2-b}B'_bO_{4-c}D_c$ (wherein, $0 \le b \le 0.5$ and $0 \le c \le 0.05$); $Li_aNi_{1-b-c}Co_bB'_cD_\alpha$ (wherein, $0.90 \le a \le 1.8$, $0 \le b \le 0.5$, $0 \le c \le 0.05$, and $0 < \alpha \le 2$); $Li_aNi_{1-b-c}Co_bB'_cO_{2-\alpha}F'_\alpha$ (wherein, $0.90 \le a \le 1.8$, $0 \le b \le 0.5$, $0 \le c \le 0.05$, and $0 < \alpha < 2$); $Li_aNi_{1-b-c}Co_bB'_cO_{2-\alpha}F'_2$ (wherein, $0.90 \le a \le 1.8$, $0 \le b \le 0.5$, $0 \le c \le 0.05$, and $0 < \alpha < 2$); $Li_aNi_{1-b-c}Mn_bB'_cD_\alpha$ (wherein, $0.90 \le a \le 1.8$, $0 \le b \le 0.5$, $0 \le c \le 0.05$, and $0 < \alpha \le 2$); $Li_aNi_{1-b-c}Mn_bB'_cO_{2-\alpha}F'_\alpha$ (wherein, $0.90 \le a \le 1.8$, $0 \le b \le 0.5$, $0 \le c \le 0.05$, and $0 < \alpha < 2$); $Li_aNi_{1-b-c}Mn_bB'_cO_{2-\alpha}F'_2$ (wherein, $0.90 \le a \le 1.8$, $0 \le b \le 0.5$, $0 \le c \le 0.05$, and $0 < \alpha < 2$); $Li_aNi_bE_cG_dO_2$ (wherein, $0.90 \le a \le 1.8$, $0 \le b \le 0.9$, $0 \le c \le 0.5$, and $0.001 \le d \le 0.1$); $Li_aNi_bCo_cMn_dGeO_2$ (wherein, $0.90 \le a \le 1.8$, $0 \le b \le 0.9$, $0 \le c \le 0.5$, $0 \le d \le 0.5$, and $0.001 \le e \le 0.1$); $Li_aNiG_bO_2$ (wherein, $0.90 \le a \le 1.8$ and $0.001 \le b \le 0.1$); $Li_aCoG_bO_2$ (wherein, $0.90 \le a \le 1.8$ and $0.001 \le b \le 0.1$); $Li_aMnG_bO_2$ (wherein, $0.90 \le a \le 1.8$ and $0.001 \le b \le 0.1$); $Li_aMn_2G_bO_4$ (wherein, $0.90 \le a \le 1.8$ and $0.001 \le b \le 0.1$); $QO_2$; $QS_2$; $LiQS_2$; $V_2O_5$; $LiV_2O_5$; $LiI'O_2$; $LiNiVO_4$; $Li_{(3-f)}J_2(PO_4)_3$ (wherein, $0 \le f \le 2$); $Li_{(3-f)}Fe_2(PO_4)_3$ (wherein, $0 \le f \le 2$); or $LiFePO_4$.

In the formula above, A may be Ni, Co, Mn, or a combination thereof; B' may be Al, Ni, Co, Mn, Cr, Fe, Mg, Sr, V, a rare earth element, or a combination thereof; D may be O, F, S, P, or a combination thereof; E may be Co, Mn, or a combination thereof; F' may be F, S, P, or a combination thereof; G may be Al, Cr, Mn, Fe, Mg, La, Ce, Sr, V, or a combination thereof; Q may be Ti, Mo, Mn, or a combination thereof; I may be Cr, V, Fe, Sc, Y, or a combination thereof; and J may be V, Cr, Mn, Co, Ni, Cu, or a combination thereof.

For example, the compound may be $LiCoO_2$, $LiMn_xO_{2x}$ (wherein, $x=1$ or 2), $LiNi_{1-x}Mn_xO_{2x}$ (wherein, $0<x<1$), $LiNi_{1-x-y}Co_xMn_yO_2$ (wherein, $0 \le x \le 0.5$, $0 \le y \le 0.5$, and $1-x-y>0.5$), or $LiFePO_4$.

A compound having a coating layer on the surface of the compound may be used, or a mixture of the compound and a compound having a coating layer may be used.

This coating layer may include a coating element compound of an oxide of a coating element, a hydroxide of a coating element, an oxyhydroxide of a coating element, an oxycarbonate of a coating element, or a hydroxycarbonate of a coating element. The compound constituting this coating layer may be amorphous or crystalline.

As the coating element included in the coating layer, Mg, Al, Co, K, Na, Ca, Si, Ti, V, Sn, Ge, Ga, B, As, Zr, or a combination thereof may be used. In the process of forming the coating layer, any suitable coating method may be used as long as this compound may be coated with such elements by a method that does not adversely affect the physical properties of the cathode active material (for example, spray coating, dipping, or the like may be used). This coating method will be understood by those skilled in the art, and therefore a detailed description thereof will be omitted.

A conductive agent, a filler, and the like may be further added to the cathode active material composition.

The conductive agent may be added in an amount of about 1 weight percent (wt %) to about 30 wt % based on the total weight of the mixture including the cathode active material. Such a conductive agent is not limited as long as it has electrical conductivity without causing a chemical change in the battery. Examples thereof may include graphite such as natural graphite or artificial graphite; carbon black, acetylene black, ketjen black, channel black, furnace black, lamp black, and summer black; conductive fibers such as carbon fiber and metal fiber; carbon fluoride; metal powder such as aluminum powder and nickel powder; conductive whiskey such as zinc oxide and potassium titanate; conductive metal oxides such as titanium oxide; and conductive agents such as polyphenylene derivatives.

The binder is a component that assists in binding of the active material and the conductive agent and binding of the active material to the current collector, and is added in an amount of about 1 wt % to about 30 wt % based on the total weight of the cathode active material composition. Examples of the binder may include polyvinylidene fluoride (PVdF), polyvinylidene chloride, polybenzimidazole, polyimide, polyvinyl acetate, polyacrylonitrile, polyvinyl alcohol, carboxymethylcellulose (CMC), starch, hydroxypropylcellulose, regenerated cellulose, polyvinylpyrrolidone, polyethylene, polypropylene, polystyrene, polymethyl methacrylate, polyaniline, acrylonitrile butadiene styrene resin, phenol resin, epoxy resin, polyethylene terephthalate, polytetrafluoroethylene, polyphenylene sulfide, polyamideimide, polyetherimide, polyether sulfone, polyamide, polyacetal, polyphenylene oxide, polybutylene terephthalate, ethylene-propylene-diene terpolymer (EPDM), sulfonated EPDM, styrene butadiene rubber (SBR), fluorine rubber, and various copolymers. The filler is a component for suppressing the expansion of the cathode, is not limited as long as it is a fibrous material not causing a chemical change in the battery, and examples thereof may include olefin polymers such as polyethylene and polypropylene; and fibrous materials such as glass fiber and carbon fiber.

As the solvent, N-methylpyrrolidone, acetone, water, or the like may be used, but the solvent is not limited thereto, and any suitable solvent for use in a lithium battery may be used. The amount of the solvent may be, for example, 10 parts by weight to 100 parts by weight based on 100 parts by weight of the cathode active material. When the amount of the solvent is within the above range, ease of formation of an active material layer is improved.

The amount of the cathode active material, the amount of the conductive agent, the amount of the filler, and the amount of the solvent are levels suitable for use in a lithium battery. The conductive agent, the filler, the binder, the solvent, or a combination thereof, may be omitted depending on the use and configuration of the lithium battery.

For example, N-methylpyrrolidone (NMP) may be used as the solvent, a PVdF or PVdF copolymer may be used as the binder, and carbon black or acetylene black may be used as the conductive agent. For example, 94 wt % of the cathode active material, 3 wt % of the binder, and 3 wt % of the conductive agent may be mixed in a powder state, NMP may be added such that solid content is 70 wt %, thus forming a slurry, and then this slurry may be coated, dried and rolled to manufacture the cathode.

The cathode current collector may have a thickness of about 3 μm to about 50 μm. This cathode current collector is not limited as long as it has suitable conductivity without causing a chemical change in the battery. For example, the cathode current collector may include stainless steel, aluminum, nickel, titanium, or fired carbon, or may include aluminum or stainless steel surface-treated with carbon, nickel, titanium or silver. The cathode current collector may form fine irregularities on its surface to increase the adhesive force of the cathode active material, and may have various forms such as film, sheet, foil, net, porous body, foam, and nonwoven fabric.

For example, the cathode may be produced by applying, drying and pressing a cathode active material on a cathode current collector. A cathode active material composition, in which a binder is mixed with a solvent, may also be prepared as needed in addition to the above-described active material. The cathode active material composition is directly applied on a metal current collector and dried to produce a cathode plate. Alternatively, the cathode active material composition may be cast onto a separate support, a film may be separated from the support, and then the separated film may be laminated on a metal current collector to produce a cathode plate.

For example, the loading level of the produced cathode active material composition may be 30 milligrams per square centimeter (mg/cm$^2$) or more, for example, 35 mg/cm$^2$ or more, and for example, 40 mg/cm$^2$ or more. Furthermore, electrode density may be 3 grams per cubic centimeter (g/cc) or more, for example, 3.5 g/cc or more.

In an embodiment, for high cell energy density, the loading level of the produced cathode active material may be about 35 mg/cm$^2$ to about 50 mg/cm$^2$, and the electrode density may be about 3.5 g/cc to about 4.2 g/cc or more.

In another embodiment, both sides of the cathode plate may be coated with the cathode active material composition at a loading level of 37 mg/cm$^2$ and an electrode density of 3.6 g/cc.

When the loading level of the cathode active material and the electrode density are within the above ranges, a battery including this cathode active material may exhibit a high cell energy density of 500 Wh/L or more. For example, the battery may exhibit a cell energy density of about 500 Wh/L to about 900 Wh/L.

Next, an anode is prepared.

For example, an anode active material composition, in which an anode active material, a conductive agent, a binder, and a solvent are mixed, may be prepared.

The anode may be prepared by directly coating an anode current collector with the anode active material composition and drying the anode active material composition. Alternatively, the anode may be prepared by casting the anode active material composition onto a separate support, separating a film from the support and then laminating the separated film on a metal current collector.

The anode active material may be, for example, a silicon containing compound, silicon oxide of formula $SiO_x$ wherein $0<x<2$, or a composite of a silicon containing compound and a carbon containing material. Here, the size (for example, average particle diameter) of silicon particles may be less than 200 nm, for example, about 10 nm to about 150 nm. The term "size" may refer to an average particle diameter when silicon particles are spherical, and may refer to an average long axis length when the silicon particles are non-spherical.

When the size of the silicon particles is within the above range, lifetime characteristics of the lithium secondary battery are improved.

The carbon containing material may be crystalline carbon, amorphous carbon, or a combination thereof. The crystalline carbon may be graphite such as natural graphite or artificial graphite of an amorphous, plate-like, flake-like, spherical or fibrous form. The amorphous carbon may be soft carbon (low-temperature fired carbon), hard carbon, mesophase pitch carbide, or fired coke.

The composite of a silicon containing compound and a carbon containing material may be a composite having a structure in which silicon particles are arranged on graphite, or a composite having a structure in which silicon particles are included on the surface of graphite and inside graphite. The composite may be, for example, an active material in which silicon (Si) particles having an average particle diameter of 200 nm or less, for example, about 100 nm to about 200 nm, and for example, 150 nm are dispersed on graphite particles and then coated with carbon, or an active material in which silicon (Si) particles exist on graphite and inside graphite. Such a composite is available as the trade name SCN1 (Si particle on Graphite) or SCN2 (Si particle inside as well as on graphite). SCN1 may be an active material obtained by dispersing silicon (Si) particles having an average particle diameter of about 100 nm to about 150 nm on graphite particles and then coating the dispersed silicon (Si) particles with carbon. SCN2 is an active material in which silicon (Si) particles having an average particle diameter of about 150 nm exist on graphite and inside graphite.

The anode active material may be used together with the above-described anode active material as long as it may be used as the anode active material of a lithium secondary battery. For example, the anode active material may be, Si, Sn, Al, Ge, Pb, Bi, Sb, a Si—Y' alloy (wherein Y may be alkali metals, alkaline earth metals, Group 13 to Group 16 elements, transition metals, transition metal oxides, rare earth elements, or a combination thereof, and wherein Y' does not comprise Si), or a Sn—Y' alloy (wherein Y' may be alkali metals, alkaline earth metals, Group 13 to Group 16 elements, transition metals, transition metal oxides, rare earth elements, or a combination thereof, wherein Y' does not comprise Sn). The element Y may be Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ge, P, As, Sb, Bi, S, Se, Te, Po, or a combination thereof.

For example, the anode active material may be lithium titanium oxide, vanadium oxide, or lithium vanadium oxide.

A conductive agent, a filler, and the like may be further added to the anode active material composition.

The binder, solvent, conductive agent and filler in the anode active material composition may be the same as those in the above-described cathode active material composition.

However, in the anode active material composition, water may be used as the solvent. For example, water may be used as the solvent, carboxymethyl cellulose (CMC), styrene butadiene rubber (SBR), an acrylate-based polymer, or a methacrylate-based polymer may be used as the binder, and carbon black, acetylene black, or graphite may be used as the conductive agent.

The amount of the anode active material, the amount of the conductive agent, the amount of the binder, and the amount of the solvent are levels suitable for use in a lithium secondary battery. The conductive agent, the binder, the solvent, or a combination thereof, may be omitted depending on the use and configuration of the lithium secondary battery.

For example, 94 wt % of the anode active material, 3 wt % of the binder, and 3 wt % of the conductive agent may be mixed in a powder state, water may be added such that solid content is 70 wt %, thus forming a slurry, and then this slurry may be coated, dried and rolled to manufacture an anode plate.

The anode current collector may have a thickness of about 3 μm to about 50 μm. This anode current collector is not limited as long as it has suitable conductivity without causing a chemical change in the battery. For example, the anode current collector may include copper, stainless steel, aluminum, nickel, titanium, or fired carbon, may include copper or stainless steel surface-treated with carbon, nickel, titanium or silver, or may include an aluminum-cadmium alloy. Similarly to the cathode current collector, the anode current collector may form fine irregularities on its surface to increase the adhesive force of the anode active material, and may have various forms such as film, sheet, foil, net, porous body, foam, and nonwoven fabric.

The loading level of the prepared anode active material composition may be set according to the loading level of the cathode active material composition.

For example, the loading level of the anode active material composition may be 12 mg/cm$^2$ or more, for example, 15 mg/cm$^2$ or more, depending on the capacity of the anode active material composition per g. Furthermore, electrode density may be 1.5 g/cc or more, for example, 1.6 g/cc or more.

In an embodiment, for high cell energy density, the loading level of the produced anode active material may be about 15 mg/cm$^2$ to about 25 mg/cm$^2$, and the electrode density may be about 1.6 g/cc to about 2.3 g/cc or more.

When the loading level of the anode active material and the electrode density are within the above ranges, a battery including this anode active material may exhibit a high cell energy density of 500 Wh/L or more or 600 Wh/L or more.

Next, a separator may be inserted between the anode and the cathode is prepared.

As the separator, any separator may be used as long as it is suitable for use in a lithium battery. A separator having low resistance to the movement of ions in the electrolyte and superior electrolyte wettability may be used. For example, the separator may include glass fiber, polyester, Teflon, polyethylene, polypropylene, polytetrafluoroethylene (PTFE), or a combination thereof, and may be made in the form of nonwoven fabric or woven fabric. For example, a windable separator including polyethylene, polypropylene, or the like may be used in a lithium ion battery, and a separator having good electrolyte impregnation ability may be used in a lithium ion polymer battery. For example, the separation film may be produced by the following method.

A polymer resin, a filler, and a solvent may be mixed to prepare a separator composition. The separator composition may be directly applied on an electrode and dried to form a separator. Furthermore, the separator composition may be cast on a support and dried, a separation film may be separated from the support, and then the separation film may be laminated on the electrode to form a separator.

The polymer resin used in the production of the separator is not limited, and any suitable material may be used as long as it may be used in a binder of an electrode plate. For example, as the polymer resin, a vinylidene fluoride/hexafluoropropylene copolymer, polyvinylidene fluoride (PVDF), polyacrylonitrile, polymethyl methacrylate, or a combination thereof may be used.

Next, the above-described electrolyte is prepared.

According to an embodiment, in addition to the above-described electrolyte, a non-aqueous electrolyte, a solid electrolyte, an organic solid electrolyte, or an inorganic solid electrolyte may be used.

As the organic solid electrolyte, for example, a polyethylene derivative, a polyethylene oxide derivative, a polypropylene oxide derivative, a phosphate ester polymer, a polyester sulfide, a polyvinyl alcohol, a polyvinylidene fluoride, or a polymer including an ionic dissociation group may be used.

As the inorganic solid electrolyte, for example, $Li_3N$, LiI, $Li_5NI_2$, $Li_3N$—LiI—LiOH, $LiSiO_4$, $Li_2SiS_3$, $Li_4SiO_4$, $Li_4SiO_4$—LiI—LiOH, or $Li_3PO_4$—$Li_2S$—$SiS_2$ may be used.

As shown in FIG. 1, the lithium secondary battery 100 includes a cathode 114, an anode 112, and a separator 113. The anode 114, the cathode 112, and the separator are wound or folded and accommodated in a battery case 120. Then, an electrolyte is injected into the battery case 120, and the battery case 120 is sealed with a cap assembly 140 to complete the lithium secondary battery 100. The battery case 120 may have a cylindrical shape, a rectangular shape, or a thin film shape. For example, the lithium secondary battery 100 may be a large-sized thin-film battery. The lithium secondary battery 100 may be a lithium ion battery.

The separator may be located between the anode and the cathode to form a battery structure. The battery structure may be laminated as a bi-cell structure and then impregnated with an electrolyte, and the resulting product may be accommodated in a pouch and sealed to complete a lithium ion polymer battery.

Further, the plurality of battery structures may be laminated to form a battery pack, and this battery pack may be used in all appliances requiring high capacity and high power. For example, the battery pack may be used in notebooks, smart phones, electric vehicles, and the like.

The lithium secondary battery according to an embodiment significantly reduces DCIR, as compared with a lithium secondary battery employing a nickel-rich lithium-nickel composite oxide as a cathode active material, and thus may exhibit improved battery characteristics.

The operating voltage of the lithium secondary battery to which the anode, the cathode and the electrolyte are applied may be, for example, about 2.5 volts (V) to about 4.4 V, for example, about 2.8 V to about 4.1 V, and energy density may be 500 Wh/L or more.

Further, the lithium secondary battery may be used in, for example, power tools operated by a power from an electric motor; electric vehicles including a hybrid electric vehicle (HEV) and a plug-in hybrid electric vehicle (PHEV); electric motorcycles including an electric bike (E-bike) and an electric scooter (E-scooter); electric golf carts; and power storage systems, but the present disclosure is not limited thereto.

As used herein, alkyl refers to fully saturated branched or unbranched (or linear or non-linear) hydrocarbons.

Non-limiting examples of "alkyl" may include methyl, ethyl, n-propyl, isopropyl, n-butyl, isobutyl, sec-butyl, n-pentyl, isopentyl, neopentyl, n-hexyl, 3-methylhexyl, 2,2-dimethylpentyl, 2,3-dimethylpentyl, and n-heptyl.

A hydrogen atom of "alkyl" may be substituted with a halogen atom, a halogen atom-substituted alkyl group of $C_1$-$C_{20}$ (for example, $CCF_3$, $CHCF_2$, $CH_2F$, or $CCl_3$), an alkoxy group of $C_1$-$C_{20}$, an alkoxyalkyl group of $C_2$-$C_{20}$, a hydroxyl group, a nitro group, a cyano group, an amino group, an amidino group, hydrazine, hydrazone, a carboxyl group or a salt thereof, a sulfonyl group, a sulfamoyl group, a sulfonic acid group or a salt thereof, phosphoric acid or a salt thereof, an alkyl group of $C_1$-$C_{20}$, an alkenyl group of $C_2$-$C_{20}$, an alkynyl group of $C_2$-$C_{20}$, a heteroalkyl group of $C_1$-$C_{20}$, an aryl group of $C_6$-$C_{20}$, an arylalkyl group of $C_7$-$C_{20}$, a heteroaryl group of $C_6$-$C_{20}$, a heteroarylalkyl group of $C_7$-$C_{20}$, a heteroaryloxy group of $C_6$-$C_{20}$, a heteroaryloxyalkyl group of $C_6$-$C_{20}$, or a heteroarylalkyl group of $C_6$-$C_{20}$.

The term "halogen" includes fluorine, bromine, chlorine, and iodine.

The "alkoxy" denotes "alkyl-O—", wherein alkyl is as described above. Examples of the alkoxy group may include a methoxy group, an ethoxy group, a 2-propoxy group, a butoxy group, a t-butoxy group, a pentyloxy group, and a hexyloxy group. An hydrogen atom of the alkoxy may be substituted with the same substituent as the above-described alkyl group.

The "alkenyl" refers to branched or unbranched hydrocarbons having at least one carbon-carbon double bond. Non-limiting examples of the alkenyl group may include vinyl, allyl, butenyl, propenyl, and isobutenyl, and a hydrogen atom of the alkenyl may be substituted with the same substituent as the above-described alkyl group.

The "alkynyl" refers to branched or unbranched hydrocarbons having a carbon-carbon triple bond. Non-limiting examples of the alkynyl may include ethynyl, butynyl, isobutynyl, and isopropynyl.

A hydrogen atom of the alkynyl may be substituted with the same substituent as the above-described alkyl group. The "aryl" includes a group in which an aromatic ring is selectively fused to one or more carbon rings. Non-limiting examples of the aryl may include phenyl, naphthyl, and tetrahydronaphthyl. A hydrogen atom of the "aryl" group may be substituted with the same substituent as the above-described alkyl group.

The "heteroaryl" refers to a monocyclic or bicyclic organic group including at least one heteroatom selected from N, O, P, or S and having carbon atoms as remaining ring atoms. The heteroaryl group may include, for example, 1 to 5 hetero atoms, and may include 5-10 ring members. The S or N may be oxidized to have various oxidation states.

Examples of the heteroaryl may include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, Isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, 2-pyrazin-2-yl, pyrazin-4-yl, pyrazin-5-yl, 2-pyrimidin-2-yl, 4-pyrimidin-2-yl, and 5-pyrimidin-2-yl.

The term "heteroaryl" includes a case where a heteroaromatic ring is fused to an aryl, cycloaliphatic, heterocyclic, or a combination thereof.

Hereinafter, the present disclosure will be described in more detail with reference to Examples and Comparative Examples. However, these Examples are for illustrating the present disclosure, and the scope of the present disclosure is not limited thereto.

EXAMPLES

Examples 1 to 5 and Comparative Examples 1 to 9

Lithium batteries were manufactured according to the components shown in Table 1 below. Each of the components was prepared as follows.
Preparation of Cathode 1
$LiNi_{0.88}Co_{0.10}Mn_{0.02}O_2$ was used as a cathode active material, carbon black was used as a conductive agent, and PVdF was used as a binder. The cathode active material, the conductive agent, and the binder were mixed with N-methylpyrrolidone (NMP) at a weight ratio of 97.7:1:1.1, and then the mixture was dispersed on an aluminum foil having a thickness of 15 μm at 33 mg/cm² per one side to coat both sides of the aluminum foil with the mixture, dried and then rolled, to prepare cathode 1 having an electrode density of 3.6 g/cc.

Preparation of Cathode 2

$LiNi_{0.88}Co_{0.08}Mn_{0.04}O_2$ was used as a cathode active material, carbon black was used as a conductive agent, and PVdF was used as a binder. The cathode active material, the conductive agent, and the binder were mixed with N-methylpyrrolidone (NMP) at a weight ratio of 97.7:1:1.1, and then the mixture was dispersed on an aluminum foil having a thickness of 12 μm at 33.58 mg/cm² per one side to coat both sides of the aluminum foil with the mixture, dried and then rolled, to prepare cathode 2 having an electrode density of 3.6 g/cc.

Preparation of Anode 1

Anode active material SSC-G (an active material designed to exhibit a capacity of 1300 mAh/g by making secondary particles containing Si of 100 nm in size and carbon-coating the secondary particles with CVD and pitch), graphite, and a binder (AG binder) were mixed with NMP at a weight ratio of 14.7:85:3, and then the mixture was dispersed on a copper foil having a thickness of 8 μm at 15.5 mg/cm² per one side to coat both sides of the copper foil with the mixture, dried and then rolled, to prepare anode 1 having an electrode density of 1.65 g/cc.

Preparation of Anode 2

SCN2 (an active material designed to exhibit a capacity of 1300 mAh/g by making secondary particles containing Si of 100 nm in size and carbon-coating the secondary particles), graphite, CMC, and SBR were mixed with NMP at a weight ratio of 13:85:1.5:0.5, and then the mixture was dispersed on a copper foil having a thickness of 15 μm at 17.25 mg/cm² per one side to coat both sides of the copper foil with the mixture, dried and then rolled, to prepare anode 2 having an electrode density of 1.65 g/cc.

Preparation of Electrolyte 1.15M $LiPF_6$, FEC/EC/EMC/DMC (volume ratio: 3/10/47/40) was used as solvent 1, 1.15M $LiPF_6$, FEC/EC/EMC/DMC (volume ratio: 5/20/35/40) was used as solvent 2, and additives given in Table 1 below are added thereto, to prepare an electrolyte.

DADPS: Diallyldiphenylsilane
DAA: Diallylamine
TAA: Triallylamine
TEA: Triethylamine
BR2: Fluorodimethyl(phenyl)silane
BR8: Fluoro(methyl)diphenylsilane
FTPhSi: fluorotriphenylsilane
HQC: 3-Hydroxy-2-quinoxalinecarboxylic acid Assembly of Lithium Battery A separator including polypropylene and having a thickness of 16 μm was interposed between the cathode and the anode, and the electrolyte was injected to manufacture a lithium battery.

Evaluation Example 1: Evaluation of Gas Generation Amount and DC Internal Resistance Each of the lithium batteries manufactured in Examples 1 to 5 and Comparative Examples 1 to 9 was charged with a current of 0.2 coulombs (C) at 25° C. until a voltage reached 3.6 V (vs. Li), and then discharged at a constant current of 0.2 until a voltage reached 2.8 V (vs. Li) (formation, $1^{st}$ cycle). Thereafter, each of the lithium batteries was charged with a current of 0.2 C until a voltage reached 4.25 V (vs. Li), and then discharged at a constant current of 0.2 until a voltage reached 2.8 V (vs. Li) (formation, $2^{nd}$ cycle). Third, each of the lithium batteries was charged with a current of 0.5 C until a voltage reached 4.25 V (vs. Li), and then cut off at a current of 0.05 C while maintaining 4.25 V of a voltage in a constant voltage mode. Then, each of the lithium batteries was discharged at a constant current of 0.2 until a voltage reached 2.8 V (vs. Li). Fourth, the third formation process was repeated (0.5 C charging/0.2 C discharging). Finally, each of the lithium batteries was charged with a current of 0.2 C until a voltage reached 4.25 V (vs. Li), and then cut off at a current of 0.05 C while maintaining 4.25 V of a voltage in a constant voltage mode.

Here, 1C charging means that the battery is charged such that the capacity (mAh) of the battery may be reached by charging for 1 hour. Similarly, 1C discharging means that the battery is discharged such that the capacity (mAh) of the battery may be completely consumed by discharging for 1 hour.

Each of the lithium batteries having been subject to the above formation processes was left at 60° C. for 10 days, and then gas generation amount and internal resistance characteristics were evaluated. The results thereof are shown in Table 1 below. DCIR at 0 days (0D) and 10 days (10D) are presented in milliohms (mΩ). The increase in DCIR (ΔDCIR) is given as a percentage.

TABLE 1

| | Electrolyte | | | | Gas generation | 0 D DCIR | 10 D DCIR | ΔDCIR |
| | Solvent | Additive | Cathode | Anode | (10 D at 60° C.) | (mΩ) | (mΩ) | (%) |
| --- | --- | --- | --- | --- | --- | --- | --- | --- |
| Ex. 1 | Solvent 1 | 0.5 wt % DADPS | Cathode 1 | Anode 1 | 0.70 | 135 | 138 | 102 |
| Ex. 2 | Solvent 1 | 0.5 wt % DAA | Cathode 1 | Anode 1 | 0.60 | 145 | 146 | 100 |
| Comp. Ex. 1 | Solvent 1 | — | Cathode 1 | Anode 1 | 0.78 | 130 | 130 | 100 |
| Comp. Ex. 2 | Solvent 1 | 0.5 wt % TAA | Cathode 1 | Anode 1 | 0.84 | 147 | 148 | 101 |
| Comp. Ex. 3 | Solvent 1 | 0.5 wt % TEA | Cathode 2 | Anode 1 | 0.98 | 120 | 132 | 110 |
| Ex. 3 | Solvent 1 | 0.3 wt % DAA | Cathode 1 | Anode 1 | 0.48 | 127 | 135 | 106 |
| Ex. 4 | Solvent 1 | 1 wt % DAA | Cathode 1 | Anode 1 | 0.76 | 136 | 148 | 109 |

TABLE 1-continued

| | Electrolyte | | Cathode | Anode | Gas generation (10 D at 60° C.) | 0 D DCIR (mΩ) | 10 D DCIR (mΩ) | ΔDCIR (%) |
|---|---|---|---|---|---|---|---|---|
| | Solvent | Additive | | | | | | |
| Ex. 5 | Solvent 1 | 2 wt % DAA | Cathode 1 | Anode 1 | 1.1 | 148 | 165 | 111 |
| Comp. Ex. 4 | Solvent 1 | — | Cathode 1 | Anode 2 | 0.38 | 179 | 251 | 140 |
| Comp. Ex. 5 | Solvent 1 | 0.1M BR8 | Cathode 1 | Anode 2 | 0.46 | 186 | 251 | 135 |
| Comp. Ex. 6 | Solvent 1 | 0.1M BR2 | Cathode 1 | Anode 2 | 0.44 | 184 | 252 | 137 |
| Comp. Ex. 7 | Solvent 1 | 0.1M FTPhSi | Cathode 2 | Anode 2 | 0.43 | 186 | 211 | 113 |
| Comp. Ex. 8 | Solvent 2 | — | Cathode 2 | Anode 1 | 0.53 | 105 | 149 | 141 |
| Comp. Ex. 9 | Solvent 2 | 0.5 wt % HQC | Cathode 2 | Anode 1 | 0.63 | 124 | 148 | 119 |

Referring to Table 1 above, it was found that the lithium batteries of Examples 1 to 5 remarkably reduce gas generation amounts, and exhibit substantially equal or smaller DCIR increase, and thus exhibit improved stability, as compared with the lithium batteries of Comparative Examples 1 to 9.

Evaluation Example 2: Evaluation of dQ/dV Characteristics

Figure 2:
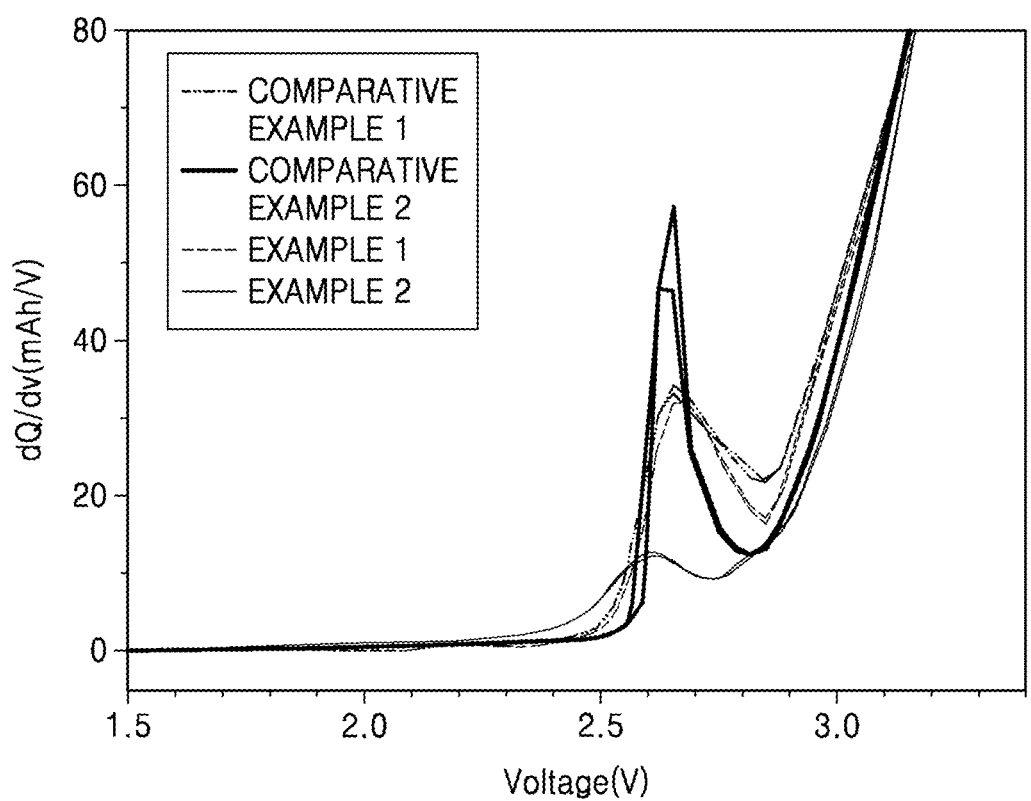
FIG. 2 is a graph of voltage (V) versus differential capacity (dQ/dV) (milliampere-hours per volt, mAh/V) obtained by differentiating a charge-discharge capacity with respect to a voltage.

FIG. 2 shows differential capacity curves obtained from a charge graph at the time of initial charging of the lithium batteries manufactured in Examples 1 and 2 and Comparative Examples 1 and 2, respectively. The differential capacity curve is a graph showing a relationship between a voltage (V) and a differential capacity (dQ/dV) obtained by differentiating a charge-discharge capacity with respect to a voltage. That is, the differential capacity curve denotes the change in a capacity of a cell per unit voltage.

Referring to FIG. 2, it was found that in the case of the lithium batteries of Examples 1 and 2, DADPS and DAA, respectively, were able to decompose before solvent molecules or reduce the decomposition of a solvent (for example, FEC). Specifically, it was found that In the case of Example 1 in which DADPS was used as an additive, the dQ/dV peak appears small as compared with the case of Comparative Example 1 in which an additive was not used, and thus the decomposition of the solvent molecules is prevented. In contrast, it was found that in the case of Comparative Example 2 in which TAA was used as an additive, the dQ/dV peak appears larger, and thus SEI deteriorates. Further, it was found that in the case of Example 2 in which DAA was used as an additive, the position of the dQ/dV peak moves as compared with the case of Comparative Example 1 in which an additive was not used, and thus DAA was decomposed before solvent molecules.

As described above, according to an embodiment, when an organic electrolyte including the diallyl compound is employed, the side reaction of the lithium battery is suppressed, and gas reduction characteristics and lifetime characteristics of the battery are improved.

It should be understood that embodiments described herein should be considered in a descriptive sense only and not for purposes of limitation. Descriptions of features or aspects within each embodiment should be considered as available for other similar features or aspects in other embodiments.

While an embodiment has been described with reference to the figures, it will be understood by those of ordinary skill in the art that various changes in form and details may be made therein without departing from the spirit and scope as defined by the following claims.

What is claimed is:
1. A lithium battery comprising:
a cathode;
an anode; and
an electrolyte between the cathode and the anode,
wherein the cathode includes a cathode active material represented by Formula 1,

$$Li_xNi_yM_{1-y}O_{2-z}A_z \qquad \text{Formula 1}$$

wherein 0.9≤x≤1.2, 0.7≤y≤0.98, and 0≤z<0.2,
M is Al, Mg, Mn, Co, Fe, Cr, V, Ti, Cu, B, Ca, Zn, Zr, Nb, Mo, Sr, Sb, W, Bi, or a combination thereof, and
A is an element having an oxidation number of −1, −2, or −3,
wherein each element of M is independently present in an amount of 0.02≤1−y≤0.3, wherein a total content of M is 0.02≤1−y≤0.3;
and
wherein the electrolyte includes a lithium salt, a non-aqueous solvent, and a diallyl compound represented by Formula 2,

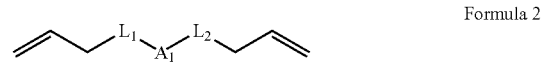

Formula 2 wherein $L_1$ and $L_2$ are each independently a single bond, a $C_1$-$C_{20}$ alkylene group, or a substituted or unsubstituted $C_2$-$C_{20}$ alkenylene group,
$A_1$ is —NH— or —Si($R_1$)($R_2$)—, and
$R_1$ and $R_2$ are each independently a hydrogen atom, or a substituted or unsubstituted $C_6$-$C_{60}$ aryl group.
2. The lithium battery of claim 1,
wherein an amount of the diallyl compound is about 0.05 parts by weight to about 5 parts by weight, per 100 parts by weight of the electrolyte.
3. The lithium battery of claim 1,
wherein the diallyl compound is a compound represented by Formula 3, Formula 4, or a combination thereof, wherein

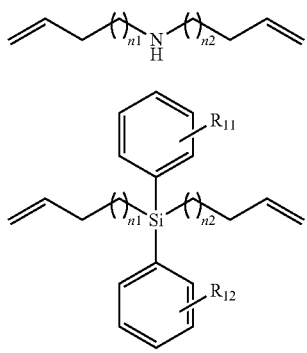

Formula 3

Formula 4 wherein, in Formulae 3 and 4, n1 and n2 are each independently an integer of 0 to 5, and $R_{11}$ and $R_{12}$ are each independently a hydrogen atom, a methyl group, an ethyl group, a propyl group, an isopropyl group, a butyl group, a sec-butyl group, a tert-butyl group, or an isobutyl group.

4. The lithium battery of claim 1,
wherein the diallyl compound is a compound represented by Formula 5, Formula 6, or a combination thereof, wherein

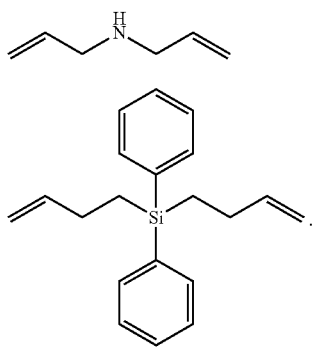

Formula 5

Formula 6

5. The lithium battery of claim 1,
wherein the lithium salt includes $LiPF_6$, $LiBF_4$, $LiCF_3SO_3$, $Li(CF_3SO_2)_2N$, $LiC_2F_5SO_3$, $Li(FSO_2)_2N$, $LiC_4F_9SO_3$, $LiN(SO_2CF_2CF_3)_2$, compounds represented by Formulae 22 to 25, or a combination thereof, wherein

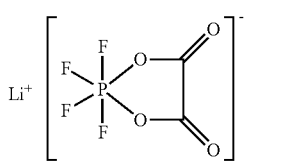

Formula 22

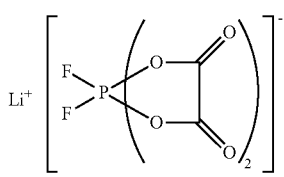

Formula 23

-continued

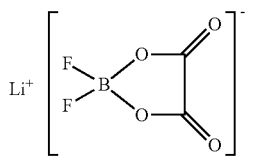

Formula 24

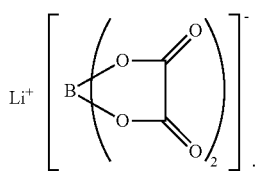

Formula 25

6. The lithium battery of claim 1,
wherein a concentration of the lithium salt in the electrolyte is about 1 molar to about 1.5 molar.

7. The lithium battery of claim 1,
wherein the non-aqueous solvent is dimethyl carbonate, diethyl carbonate, ethyl methyl carbonate, dipropyl carbonate, methyl propyl carbonate, ethyl propyl carbonate, ethylene carbonate, propylene carbonate, butylene carbonate, methyl propionate, ethyl propionate, propyl propionate, tetraethylene glycol dimethyl ether, or a combination thereof.

8. The lithium battery of claim 1,
wherein the electrolyte comprises a cyclic carbonate compound, a cyclic acid anhydride compound, a phosphorus containing compound, a sulfur containing compound, or a combination thereof.

9. The lithium battery of claim 8,
wherein the electrolyte includes a cyclic carbonate compound, a cyclic acid anhydride compound, or a combination thereof, and
the diallyl compound has a reduction potential which is greater than a reduction potential of cyclic carbonate compound or a reduction potential of the cyclic acid anhydride compound.

10. The lithium battery of claim 9,
wherein an amount of the cyclic carbonate compound, the cyclic acid anhydride compound, or the combination thereof is about 0.1 parts by weight to about 30 parts by weight, per 100 parts by weight of the electrolyte.

11. The lithium battery of claim 8,
wherein the cyclic carbonate compound is fluoro-ethylene carbonate, vinylene carbonate, vinyl ethylene carbonate (VEC), or a combination thereof, and
wherein the cyclic acid anhydride compound is maleic anhydride, succinic anhydride, or a combination thereof.

12. The lithium battery of claim 8,
wherein the phosphorus containing compound is a phosphine compound, a phosphate compound, a phosphite compound, or a combination thereof, and
wherein the sulfur containing compound is a sulfone compound, a sulfonate compound, a sultone compound, a disulfonate compound, or a combination thereof.

13. The lithium battery of claim 1,
wherein, in Formula 1, y satisfies $0.8 \leq y \leq 0.98$.

14. The lithium battery of claim 1,
wherein, in Formula 1, M is Co, Mn, or a combination thereof.

15. The lithium battery of claim 1,
wherein the cathode active material is represented by Formula 7 or 8, wherein $$Li_{x'}Ni_{y'}Co_{1-y'-z'}Al_{z'}O_2 \qquad \text{Formula 7}$$

$$Li_{x'}Ni_{y'}Co_{1-y'-z''}Mn_{z''}O_2 \qquad \text{Formula 8}$$

wherein, in Formulae 7 and 8, x', y', and z' are each independently $0.9 \leq x' \leq 1.2$, $0.88 \leq y' \leq 0.98$, $0 < z' < 0.1$, and $0 < 1-y'-z' < 0.12$.

16. The lithium battery of claim 1,
wherein the cathode active material comprises $Li_{1.02}Ni_{0.88}Co_{0.08}Mn_{0.04}O_2$, $Li_{1.02}Ni_{0.88}Co_{0.10}Mn_{0.02}O_2$, $Li_{1.02}Ni_{0.91}Co_{0.06}Mn_{0.03}O_2$, $LiNi_{0.94}Co_{0.04}Mn_{0.02}O_2$, $LiNi_{0.88}Co_{0.10}Mn_{0.02}O_2$, $LiNi_{0.88}Co_{0.08}Mn_{0.04}O_2$, $Li_{1.02}Ni_{0.88}Co_{0.08}Al_{0.04}O_2$, $Li_{1.02}Ni_{0.88}Co_{0.10}Al_{0.03}O_2$, $Li_{1.02}Ni_{0.91}Co_{0.06}Al_{0.03}O_2$, $LiNi_{0.94}Co_{0.04}Al_{0.02}O_2$, or a combination thereof.

17. The lithium battery of claim 1,
wherein the anode includes an anode active material, and
wherein the anode active material comprises a silicon containing compound, a carbon containing compound, a composite of a silicon containing compound and a carbon containing compound, a silicon oxide of the formula $SiO_{x1}$ wherein $0 < x1 < 2$, or a combination thereof.

18. The lithium battery of claim 17,
wherein the anode active material comprises a silicon containing compound or a silicon oxide, and
wherein the silicon containing compound comprises silicon particles with an average particle diameter of 200 nanometers or less.

19. The lithium battery of claim 1,
wherein the lithium battery has a capacity retention of 75% or more after 200 cycles of charging and discharging at 25° C.

20. The lithium battery of claim 1, wherein the lithium battery has a cell energy density of 500 watt-hours per liter or more.

* * * * *